(12) United States Patent
Schmidt et al.

(10) Patent No.: US 6,206,004 B1
(45) Date of Patent: *Mar. 27, 2001

(54) TREATMENT METHOD VIA THE PERICARDIAL SPACE

(75) Inventors: Cecil C. Schmidt, Edina, MN (US); Robert A. Kloner, Toluca Lake, CA (US)

(73) Assignee: Comedicus Incorporated, Columbia Heights, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/762,379

(22) Filed: Dec. 6, 1996

(51) Int. Cl.$^7$ ..................................................... A61B 19/00
(52) U.S. Cl. ........................................... 128/898; 604/500
(58) Field of Search ................................ 604/52, 53, 96, 604/4, 33, 28, 21, 117; 128/898; 607/120

(56) References Cited

U.S. PATENT DOCUMENTS

| | | |
|---|---|---|
| 3,923,060 | 12/1975 | Ellinwood, Jr. . |
| 4,003,379 | 1/1977 | Ellinwood, Jr. . |
| 4,531,935 * | 7/1985 | Berryessa ........................ 604/53 X |
| 4,991,578 | 2/1991 | Cohen . |
| 5,213,570 | 5/1993 | VanDeripe . |
| 5,220,917 | 6/1993 | Cammilli et al. . |
| 5,269,326 | 12/1993 | Verrier . |
| 5,336,252 | 8/1994 | Cohen . |
| 5,358,481 * | 10/1994 | Todd et al. ........................ 604/52 X |
| 5,387,419 | 2/1995 | Levy et al. . |
| 5,452,733 | 9/1995 | Sterman et al. . |
| 5,505,698 * | 4/1996 | Booth et al. ........................ 604/96 |
| 5,634,895 | 6/1997 | Igo et al. . |
| 5,662,607 * | 9/1997 | Booth et al. ........................ 604/96 |
| 5,681,278 | 10/1997 | Igo et al. . |
| 5,702,358 * | 12/1997 | Witherspoon et al. ................ 604/4 |
| 5,735,290 * | 4/1998 | Sterman et al. ...................... 128/898 |
| 5,762,868 * | 6/1998 | Leonard ............................. 604/4 X |

FOREIGN PATENT DOCUMENTS

WO 96/40368    12/1996   (WO) .

OTHER PUBLICATIONS

Product Description Sheet by Comedicus Incorporated for A New Approach: Access The Pericardial Space With The PerDUCER™ Pericardial Access Device Date ?.
Medical Device & Diagnostic Industry, Advertisement, "Spectrum . . . precision from start to finish" Date ?.
Advertisement"Corrosion–Resistant Alloys", Ulbrich Stainless Steels & Special Metals Inc Date ?.
Surgical Instruments, Advertisement for T.A.G. Medical Products Ltd Date ?.

* cited by examiner

Primary Examiner—David J. Isabella
Assistant Examiner—Kelly O'Hara
(74) Attorney, Agent, or Firm—Merchant & Gould P.C.

(57) ABSTRACT

A method for treating the heart and associated vessels and tissues, by controlling the temperature of the pericardial space and/or introducing therapeutic agents, drugs or the like thereto, includes providing a fluid, liquid(s), gas(es) or mixtures thereof, with or without therapeutic agents, drugs or the like, and heating and/or cooling, this fluid. At a time proximate to the heating and/or cooling of the fluid, the pericardial space is accessed by pericardiocentesis, such that the pericardium is punctured and the pericardial space is instrumentized at a location, and in particular, a location where treatment is desired. The heated and/or cooled fluid is then delivered to the pericardial space. At a time after delivery, the fluid is withdrawn from the pericardium, through either the same catheter, or through another catheter at different point along the pericardium, that was also instrumentized (catheterized) by standard pericardiocentesis procedures. This delivery and withdrawal of the fluid may be coordinated, so as to form a circuit.

11 Claims, 4 Drawing Sheets

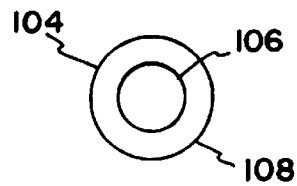
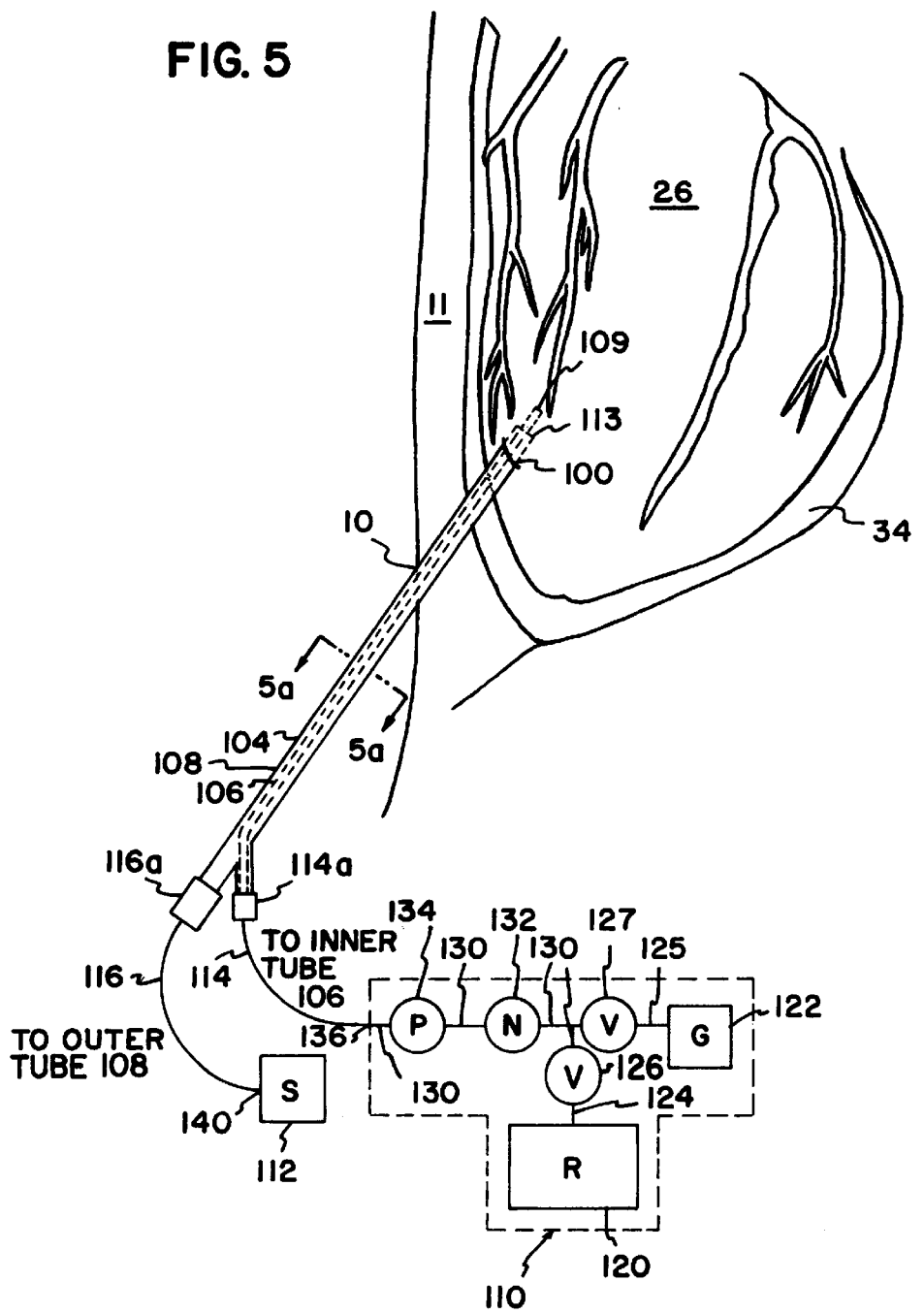

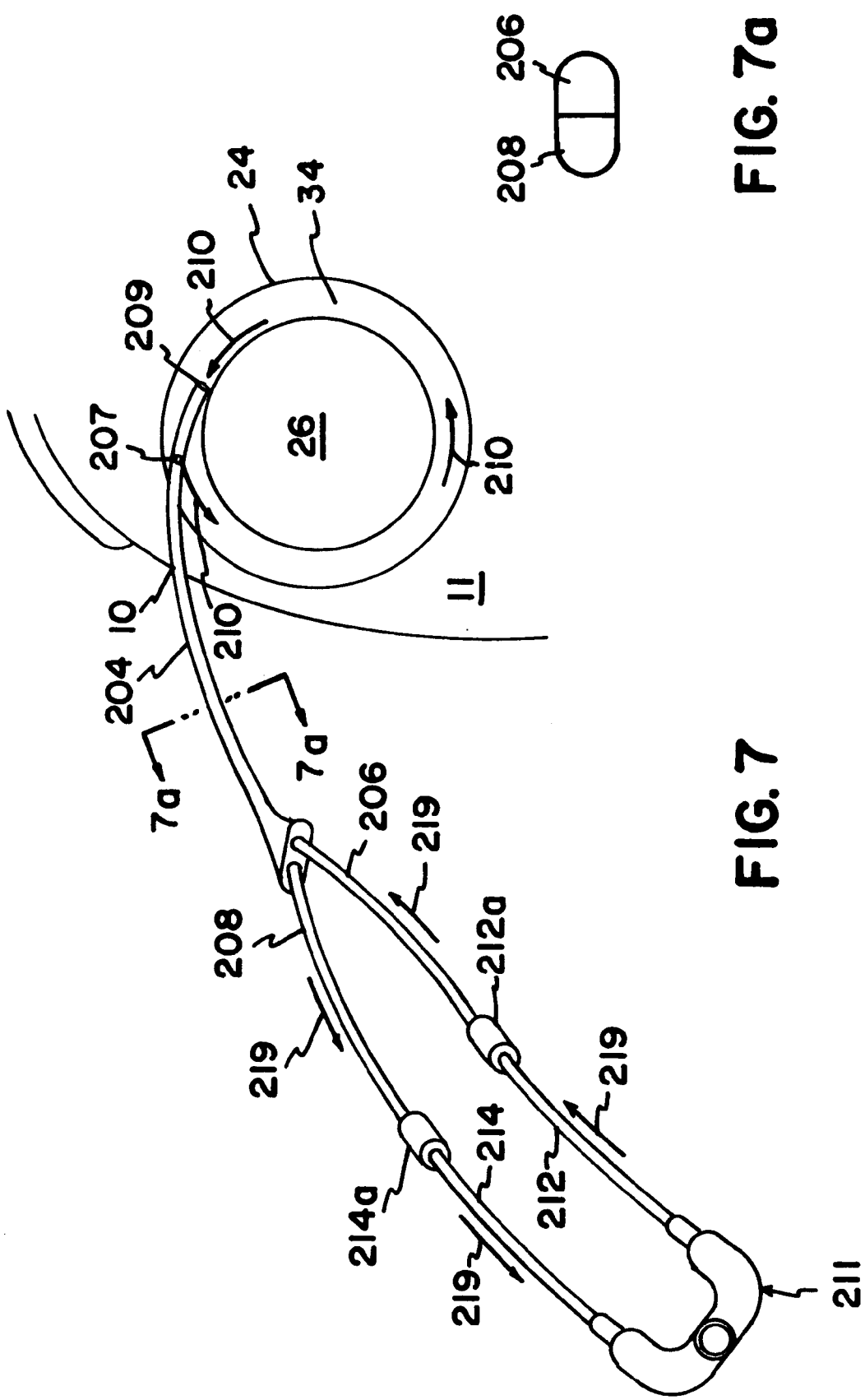

TREATMENT METHOD VIA THE PERICARDIAL SPACE

FIELD OF THE INVENTION

The present invention is directed to treating the heart muscle and associated coronary vessels by controlling the temperature of the pericardial space. More particularly, the present invention includes accessing the pericardial space by puncturing the pericardium (pericardial sac) without injuring the heart and associated coronary vessels, delivering and withdrawing the heated and/or cooled fluids for controlling the temperature of the pericardial space.

BACKGROUND OF THE INVENTION

Knowledge of the pericardium (pericardial sac) dates back to the time of Galen (129–200 A.D.) the Greek physician and anatomist who created the term "pericardium." The pericardium is a conical membranous sac in which the heart and the commencement of the great vessels are contained. *Gray's Anatomy* (1977 ed.) pp. 457–460. The pericardium is fluid-filled and functions to prevent dilatation of the chambers of the heart, lubricates the surfaces of the heart, and maintains the heart in a fixed geometric position. It also provides a barrier to the spread of infection from adjacent structures in the chest cavity and prevents surrounding tissue(s) from adhering to the heart. The space between the pericardium and the heart, known as the pericardial space, is normally small in volume and the fluid film within it is too thin to functionally separate the heart and the pericardium. It has been observed that when fluid is injected into the pericardial space, it accumulates in the atrioventricular and interventricular grooves, but not over the ventricular surfaces. See, Shabetai R., "Pericardial and Cardiac Pressure", *Circulation,* 77:1 (1988).

Pericardiocentesis, or puncture of the pericardium, heretofore has been performed for; 1) diagnosis of pericardial disease(s) by study of the pericardial fluid; 2) withdrawal of pericardial fluid for the treatment of acute cardiac tamponade; and 3) infusion of therapeutic agents for the treatment of malignant effusion or tumors. During 1994, it was estimated that approximately 12,000 pericardiocentesis procedures were performed in the United States and that less than 200 of these patients underwent therapy with the intrapericardial injection of drugs. At present, intrapericardial injection of drugs is clinically limited to the treatment of abnormal pericardial conditions and diseases, such as malignant or loculated pericardial effusions and tumors. Drugs that have been injected into the pericardial space include antibiotic (sclerosing) agents, such as tetracycline, bleyomycin and streptokinase.

Intrapericardial drug delivery has not been clinically utilized for heart-specific treatments where pericardial pathology is normal, because the pericardial space is normally small and very difficult to access without invasive surgery or risk of cardiac injury by standard needle pericardiocentesis techniques. Normally, pericardiocentesis procedures are carried out by highly specialized, experienced personnel in the cardiac catheterization laboratory of medical facilities, assisted by fluoroscopy and electrocardiogram monitoring equipment.

Electrocardiographic monitoring of the procedure using the pericardial needle as an electrode is commonly employed, as disclosed in Bishop L. H., et al., "The Electrocardiogram as a Safeguard in Pericardiocentesis", in *JAMA,* 162:264 (1956), and Neill J. R., et al., "A Pericardiocentesis Electrode", in *The New England Journal of Medicine,* 264:711 (1961); Gotsman M. S., et al. "A Pericardiocentesis Electrode Needle", in *Br. Heart J.,* 28:566 (1966); and Kerber R. E., et al., "Electrocardiographic Indications of Atrial Puncture During Pericardiocentesis", in *The New England Journal of Medicine,* 282:1142 (1970). An echocardiographic transducer with a central lumen has also been used to guide the pericardiocentesis needle, as reported in Goldberg B. B., et al., "Ultrasonically Guided Pericardiocentesis", in *Amer. J. Cardiol.,* 31:490 (1973).

However, there are complications associated with needle pericardiocentesis. These complications include laceration of a coronary artery or the right ventricle, perforation of the right atrium or ventricle, puncture of the stomach or colon, pneumothorax, arrhythmia, tamponade, hypertension, ventricular fibrillation, and death. Complication rates for needle pericardiocentesis are increased in situations where the pericardial space and fluid effusion volume is small (i.e. the pericardial size is more like normal).

U.S. Pat. No. 5,071,428 (Chin, et al.) discloses a method and apparatus for accessing the pericardial space for the insertion of implantable defibrillation leads. This method requires gripping the pericardium with a forceps device and cutting the pericardium with a scalpel (pericardiotomy) under direct vision through a subxiphoid surgical incision.

Uchida Y., et al., "Angiogenic Therapy of Acute Myocardial Infarction by Intrapericardial Injection of Basic Fibroblast Growth Factor and Heparin Sulfate", in *Circulation AHA Abstracts* (1994) reported a method for the intrapericardial injection of angiogenic agents. While not described in detail, this method generally involved the percutaneous transcatheter bolus injection of drugs into the pericardial cavity via the right atrium. A major drawback of this method is that the right atrial wall is crossed, that could lead to bleeding into the pericardial space. In addition, the method involved the bolus injection of drugs rather than long-term delivery via a catheter or controlled release material.

SUMMARY OF THE INVENTION

The present invention improves on the prior art by providing a method for heating and/or cooling the pericardial space for controlling the temperature therein, for efficiently delivering therapeutic agents, drugs or the like, to the pericardial space for treating the heart and associated vessels and tissues and for thermally shocking or heating the heart without the contemporaneous delivery of drugs. This agent delivery approach, directly into the pericardial space allows for lower doses of these therapeutic agents, drugs, or the like, longer duration of these agents, less toxicity and improved effectiveness (absorption).

The method of the present invention is accomplished by providing a fluid (liquid(s), gas(es) or mixtures thereof), for example water, sterile saline, lactated Ringer's Solution that may optionally or preferably include therapeutic agents, drugs or the like, such as thrombolitic agents, nitric oxide donors, coronary vasodilators, oxygen radical scavengers, platelet inhibitors, and heating and/or cooling, this fluid, relative to normal body temperature (approximately 37° C.). At a time proximate to the heating and/or cooling of the fluid, the pericardial space is accessed by pericardiocentesis, such that the pericardial space is instrumentized at a location, and in particular, a location where treatment is desired. The heated and/or cooled fluid is then delivered to the pericardial space, and at a time after delivery, is withdrawn from the pericardium, through either the same catheter, or through a different opening in the pericardium, also created by standard pericardiocentesis procedures, and instrumentized similarly. This delivery and withdrawal of the fluid may be coordinated, so as to form a circuit, and subsequent deliveries and withdrawals are continued for as long as desired to achieve the requisite effects. The delivery and withdrawal of the fluid can be from the same or separate points along the pericardium and can be done in batched, continuous, intermittent or pulsed manners, and heating and cooling can be used together (e.g., heating followed by cooling).

BRIEF DESCRIPTION OF THE DRAWINGS

The present invention will be described with reference to the accompanying drawings, wherein like reference numerals identify corresponding or like components.

In the Drawings:

FIG. 5 is an embodiment of the method of the present invention;

FIG. 5a is a cross sectional view of the catheter employed in performing the method of the present invention taken along line 5a—5a of FIG. 5;

FIG. 7 is a third embodiment of the method of the present invention; and

FIG. 7a is a cross sectional view of the catheter employed in performing the method of the present invention taken along line 7a—7a of FIG. 7.

DETAILED DESCRIPTION OF THE DRAWINGS

The method of the present invention initially involves accessing the pericardial space. This is typically accomplished by a procedure, known as pericardiocentesis. In the present invention, it is preferred to perform this pericardiocentesis procedure, to access the pericardial space of the heart, using an instrument available under the name PerDUCER™ pericardial access device, available from Comedicus Incorporated, 3839 Central Avenue, NE, Columbia Heights, Minn. 55421, and described in "A New Approach: Access the Pericardial Space with the PerDUCER™ Pericardial Access Device" from Comedicus Incorporated, this literature being incorporated by reference herein.

While only one instrument and method for accessing the pericardial space is shown in FIGS. 1–4 and described below, other instruments and methods are also permissible to access the pericardial space.

Figure 1:
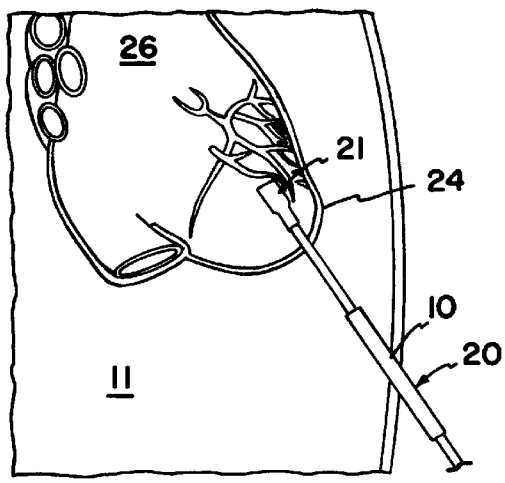
FIGS. 1–4 show a method of pericardiocentesis for accessing the pericardial space to perform the method of the present invention.
Figure 2:
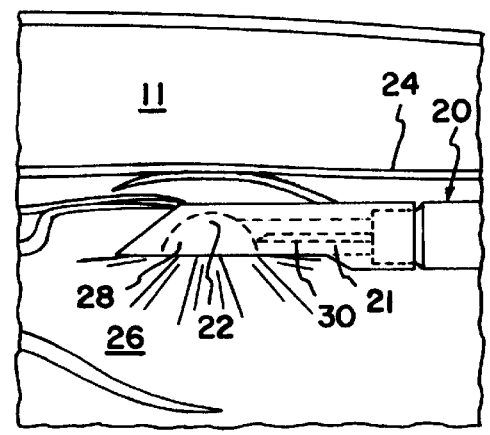

As shown in FIG. 1, a small subxiphoid incision 10 is made in the skin into the chest cavity 11 of a patient. A standard Mediastinscopy endoscope (not shown) is inserted into this incision for direct vision and the apparatus 20 having an end 21 with a suction dome 22 is inserted through the endoscope, to the pericardium 24 surrounding the heart 26.

Once the dome 22 of the apparatus 20 is at a point proximate the tissue of the pericardium 24, and in particular, over the anterior surface of the pericardium 24, suction is applied, creating a lifted section or "bleb" 28 of pericardium tissue. This bleb 28 of pericardium 24 tissue is secured in the suction dome 22 for puncture and subsequently punctured by a retractable needle 30 having limited travel to prevent laceration of the heart 26.

Figure 3:
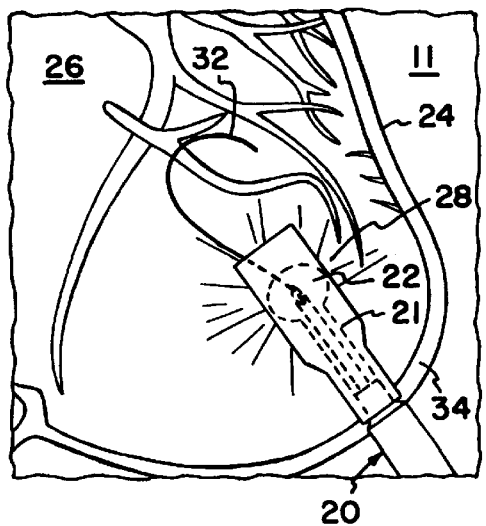
Figure 4:
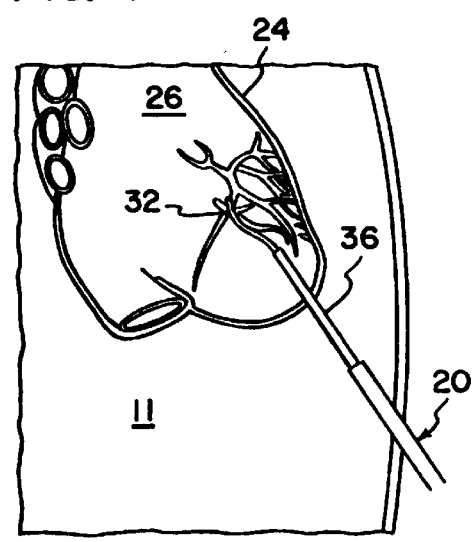

Once punctured by the needle 30, a guidewire 32 is passed through the needle 30 into the bleb 28 and into the pericardial space 34, as shown in FIG. 3. A catheter 36, preferably, a single or multiple lumen catheter, is then slid over the guidewire 32 to the requisite placement within the pericardial space 34, as shown in FIG. 4. The access apparatus 20 is ultimately removed from the chest cavity 11 and subsequently from the operating field.

Once the pericardial space 34 has been catheterized, fluids (liquids, gases, or mixtures thereof) may be introduced and withdrawn from the pericardial space 36. These fluids will be heated and cooled, this heating and cooling relative to normal body temperature (approximately 37° C.), prior to their delivery, and may be delivered and withdrawn at varying speeds in many different modes (e.g., continuous, intermittent, etc.), depending upon the particular treatment or effect desired.

Turning now to FIGS. 5 and 5a, there is shown a method of the invention for controlling the temperature in the pericardial space 34 of the pericardium 24 of the heart 26, where only a single incision 100 (from a needle puncturing the tissue of the pericardium 24), was made in the pericardium 24 for accessing the pericardial space 34. In accordance with the pericardiocentesis procedure described above, a double lumen catheter 104, preferably of concentric inner 106 and outer 108 tubes (shown partially in broken lines) has been introduced into the pericardial space 34 by the apparatus 20 (FIGS. 1–4).

The inner tube 106 functions to deliver fluid (liquid, gas, or mixtures thereof), through an opening 109, that may or may not contain drugs or other therapeutic agents, from the fluid source 110 to the pericardial space 34, while the outer tube 108, in communication with a suction source 112, functions to facilitate the withdrawal of fluid from the pericardial space 34, through an opening 113. The inner tube 106 preferably connects to the fluid source 110 by a detachable line(s) 114 at a connector 114a and the outer tube 108 preferably connects to the suction source 112 by a detachable line(s) 116 at a connector 116a. It is preferred that the catheter 104 have the inner (fluid delivery) tube 106 extend beyond the outer (fluid withdrawal) tube 108, for projecting further into the pericardial space 34 to prevent fluid from immediately returning into the catheter 104. The connectors 114a, 116a employed here, as well as those connectors (168a, 170a in FIG. 6 and 212a, 214a in FIG. 7) in the systems described below are standard, medical grade connectors, such as Luer-Lock™ connectors. Other equivalent connectors are also suitable.

The fluid source 110 includes a reservoir 120 for liquids and a gas source 122 for gases. Both the reservoir 120 and the gas source 122 include conduits 124, 125, through which the respective liquid or gas is transported to the respective valves 126, 127. An outflow conduit 130 extends from the valve 126, and passes through a heat exchanger 132, for heating and/or cooling the fluid in the conduit 130, and a pump 134, for delivering fluid to the pericardium. The conduit 130 terminates in a port 136, to which the line 114 attaches, by standard connection techniques (e.g., plug-type fits).

The reservoir 120 is designed to hold liquids, such as water, sterile saline, lactated Ringer's Solution, therapeutic agents, drugs or the like, such as such as thrombolitic agents nitric oxide donors, coronary vasodilators, beta blockers, oxygen radical scavengers, platelet inhibitors, or mixtures thereof. The reservoir 120 may be surrounded by heating and/or cooling means, and if so, the fluid source 110 need not include the heat exchanger 132. The gas source 122, typically includes gases such as nitrogen, nitric oxide, and mixtures thereof. Alternately, either the reservoir 120 or gas source 122, or both, may be attached to the fluid source 110 at the time of use. Additionally, fluid (liquid, gas or mixtures thereof) could be placed directly into the inner (fluid delivery) tube 106 or its line 114 and/or fluid could be withdrawn directly from the outer (fluid withdrawal) tube 108 or line 116.

The valves 126, 127 are preferably two way valves, that are controllable either manually or automatically, to regulate precise amounts of liquid and gas. If automatic, the valves 126, 127 can be subject to microprocessor control.

The heat exchanger 132 is capable of both heating and cooling the fluid passing through the outflow conduit 130, and if required, can alternately heat and cool the fluid passing through the heat exchanger 132. The heat exchanger 132 can be manually or automatically controlled, and if automatically controlled, may be done so by a microprocessor.

The pump 134 preferably includes an internal valve (not shown) to assist in its control, and is capable of pumping at various speeds and in continuous and intermittent modes and is adjustable to various pressures. The intermittent modes can be timed or pulsatile. Moreover, the pump 134 is also capable of pumping in reverse. The pump 134 may be manually or automatically controlled, and automatic control may be done with a microprocessor, to ensure proper fluid delivery, circulation therein and subsequent withdrawal from, of fluid in the pericardial space 34.

The suction source 112 includes a port 140 for receiving the line 116, that attaches to the outer (fluid withdrawal) tube 108. This suction source 112 may include pumps, valves or the like and may be manually or automatically controlled. Automatic control includes microprocessor control, such that the actions of the valves 126, 127, heat exchanger 132, pump 134 and suction source 112 are integrated and coordinated by the microprocessor.

Alternately, a line, with or without a pump along it, as well as additional devices, such as filters, for treating the withdrawn fluid prior to its return to the reservoir 120, could be connected from the suction source 112 to the reservoir 120 of the fluid source 110 to make a circuit. In this way fluid could be treated (for recycling) and subsequently returned to the pericardial space 34. This cycling could continue for as long as desired.

Monitoring devices (not shown), such as those for pressure or temperature, i.e., feedback sensors, may be placed along the outflow conduit 130, along the inner tube 106 or outer tube 108 of the catheter 104, or in the pericardial space 34, to monitor the fluid pressure and/or temperature at the requisite locations. If the system includes a microprocessor, the feedback sensors may be connected to the microprocessor for ultimately controlling the system components (e.g., valves, pumps, heat exchanger, etc.), as detailed above.

It is preferred that the movement(s) of the pump 134, for delivering fluid into the pericardial space 34, heating and cooling of the fluid by the heat exchanger 132 and suction from the suction source 112, for withdrawing the fluid from the pericardial space 34, be coordinated to ensure proper fluid circulation within the pericardial space 34 for proper temperature control and treatment. For example, the withdrawal by the suction source 112 could be coordinated with the fluid delivery process as one or several pulses of fluid could be accompanied by a pulse of suction. Also, suction could be timed at predetermined intervals following a predetermined timed fluid delivery. Additionally, a delivery/withdrawal of heated fluid could be followed by a delivery/withdrawal of cooled fluid. These deliveries followed by withdrawal (suction) patterns may be repeated for as long as desired to accomplish the requisite treatment. Other similar fluid delivery and suction (withdrawals) are also permissible and may be coordinated as desired.

In another example, it is desired to facilitate heat transfer in the pericardial space 34. Here, a pericardiocentesis is performed, and the pericardial space 34 is catheterized with the above described double lumen catheter, in accordance with the above-described procedure. A solution of TriNORx™ compound (in a nitric oxide donor) in the reservoir of a fluid source would be heated by either, heating the reservoir or passing the solution through the heat exchanger. The now warmed solution would be pumped through the inner (fluid delivery) tube into the pericardial space 34. The pumping could be at various speeds and in continuous or intermittent modes, e.g., pulsatile, to deliver warm fluid to the pericardial space 34, allowing for heat transfer to the cooler heart 26. Fluid withdrawal would be by suction, as the suction provided by a suction source, would be coordinated with the pumping, such that approximately equal amounts of fluid delivered to the pericardial space 34 would be withdrawn therefrom.

Figure 6:
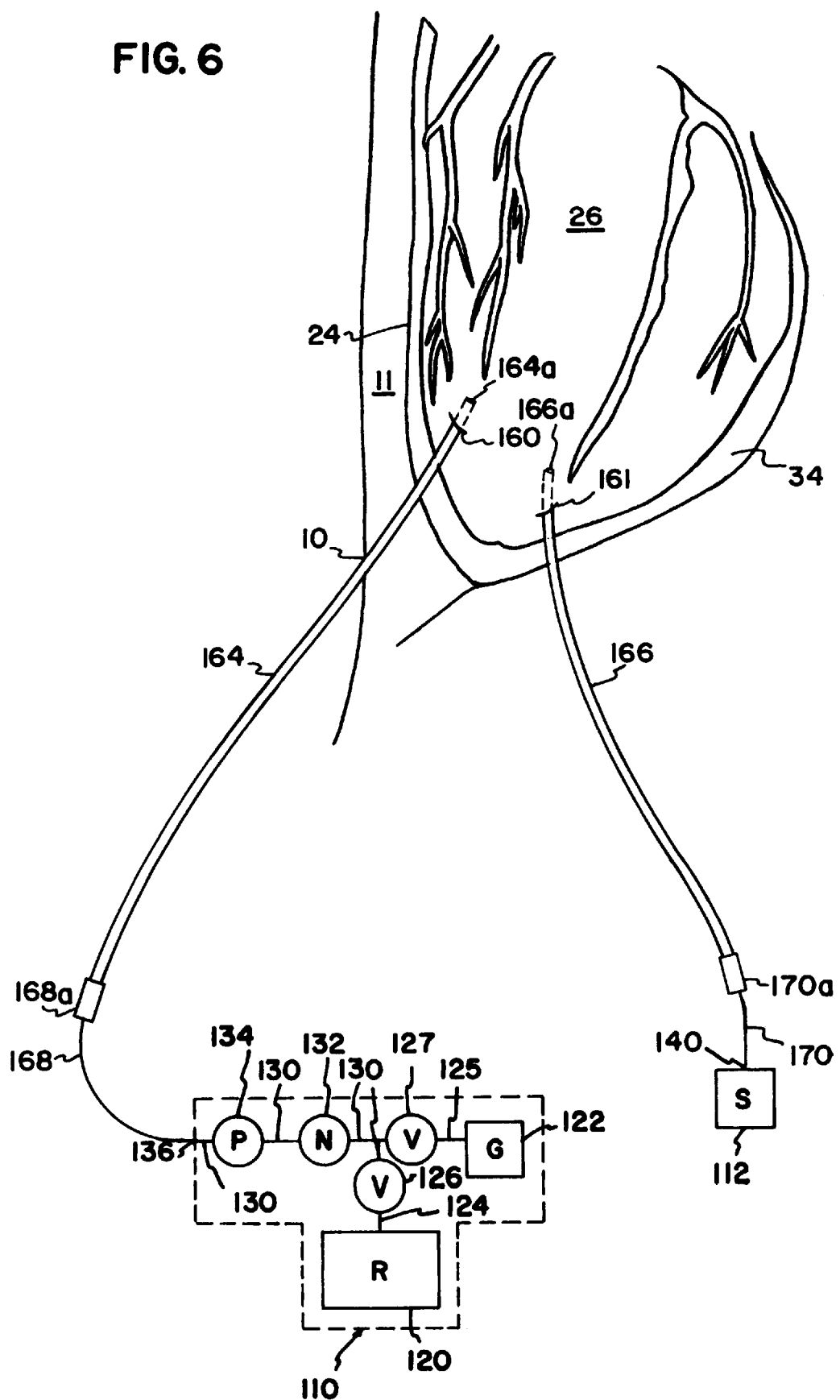
FIG. 6 is a second an embodiment of the method of the present invention.

FIG. 6 shows another embodiment of the method of the present invention. This embodiment differs from that shown above (in FIGS. 5 and 5a), in that separate entries 160, 161 to the pericardial space 34 are provided by pericardiocentesis (described above) for fluid delivery 160 and fluid withdrawal 161, to and from the pericardial space 34. Additionally, different instrumentation is required as a result of instrumentizing two separate incisions 160, 161 in the pericardial space 34.

It is preferred that these incisions 160, 161 be instrumentized (e.g., catheterized) with single lumen catheters 164, 166 (shown partially in broken lines in the pericardial space 34), with a delivery catheter 164 is used to deliver fluid through an opening 164a, while a withdrawal catheter 166 is used to withdraw fluid through an opening 166a, respectively, to and from the pericardial space 34. The delivery catheter 164 attaches to a line 168 at a connector 168a, that connects to the fluid source 110, while the withdrawal catheter 166 connects to a line 170 at a connector 170a, that connects to the suction source 112.

Alternately, either the reservoir 120 or gas source 122, or both, may be attached to the fluid source 110 at the time of use. Additionally, fluid (liquid, gas or mixtures thereof) could be placed directly into the fluid delivery catheter 164 or its line 168 and/or fluid could be withdrawn directly from the withdrawal catheter 166 or its 170.

Additionally, monitoring devices (not shown), such as those for pressure or temperature, i.e., feedback sensors, may be placed along the lines or along the catheters to monitor the pressure and/or temperature along the fluid delivery or withdrawal pathways. Alternately, a line, with or without a pump along it, as well as additional devices, such as filters for treating the withdrawn fluid prior to its return to the reservoir 120, could be connected from the suction source 112 to the reservoir 120 of the fluid source 110 to make a circuit. In this way fluid could be treated (for recycling) and subsequently returned to the pericardial space 34. This cycling could continue for as long as desired.

FIGS. 7 and 7a are similar to FIGS. 5 and 5a above in that there is shown a method for controlling pericardial space 34 temperature and/or treatment involving a single puncture of the pericardium 24, by the methods described above, for accessing the pericardial space 34 and creating a circuit for fluid transport. The pericardial space 34 is catheterized with a double lumen catheter 204, in accordance with the methods described above. The catheter 204 has a first (fluid delivery) tube 206 for delivering fluid to the pericardial space 34, through an opening 207, and a second (fluid withdrawal) tube 208, extending beyond the first tube 206, for withdrawing fluid from the pericardial space 34, through an opening 209. This arrangement creates a circulation in the pericardial space 34 in the direction of arrows 210.

A cooling pump 211 connects by lines 212, 214, at connectors 212a, 214a, to the first 206 and second 208 tubes, forming a circuit. Fluid, for example, water, saline, or other fluid solutions including therapeutic agents, drugs or the like, or gases, or mixtures thereof (as discussed above), from a fluid source (not shown) is then introduced through a line (not shown) into this circuit, preferably at the cooling pump 211. Alternately, fluid can be delivered to or withdrawn directly from the first 206 and second 208 tubes and/or lines 212, 214.

The cooled fluid, preferably cooled to approximately 0° C. (just above freezing) to 25° C., by the cooling pump, in order to cool the heart approximately 2–3° C. below normal body temperature, is delivered, circulated in, and ultimately withdrawn from the pericardial space 34. The direction of this fluid transport is indicated by arrows 219. The fluid circulating in the pericardial space 34 cools the heart 26, in order to decrease the oxygen demand of the heart, and reduce heart attach size or possibly prevent a heart attack. Additionally, this might also reduce the chest pain associated with unstable angina pectoris. The cooling pump 211 preferably includes a valve (not shown) to release fluid from the circuit if necessary. The cooling pump 211 is capable of pumping in various speeds and modes (continuous and/or intermittent, as discussed above). Alternately, this cooling pump 211 could be a heating pump or a heating/cooling pump for providing therapy involving heating fluid as well as both heated and cooled fluid.

While embodiments of the present invention have been described so as to enable one skilled in the art to practice the techniques of the present invention, the proceeding description is intended to be exemplary. It should not be used to limit the scope of the invention, that should be determined by reference to the following claims.

What is claimed is:

1. A method of treating a patient's heart by application of a cooled fluid to a pericardial surface of said heart from a pericardial space of said patient's heart, said method comprising:

a. accessing said pericardial space by:
      1. lifting a section of pericardium surrounding said pericardial space to create a bleb; and
      2. puncturing through said bleb of pericardium with a retractable needle;
   b. delivering to said pericardial space said cooled fluid to contact said pericardial surface of said heart to treat said heart.

2. The method of claim 1, wherein said delivering step includes pumping said fluid into said pericardial space in at least one pulse.

3. The method of claim 1, wherein said cooled fluid includes drugs, therapeutic agents or mixtures thereof.

4. The method of claim 1, wherein said fluid is first heated and then cooled.

5. The method according to claim 1 wherein said section of pericardium is lifted by suction.

6. The method according to claim 5 wherein said cooled fluid is delivered to said pericardial space by passing a catheter into said pericardial space at a first location to deliver said cooled fluid to said pericardial space.

7. The method of claim 6, wherein said catheter includes a double lumen catheter, having an inner lumen formed by a first tube and an outer lumen formed by a second tube, said first and second tubes concentric to each other, said second tube being longer than said first tube, said first tube for providing suction of said fluid and said second tube for delivering said fluid to the pericardial space.

8. The method according to claim 6 wherein a second catheter is inserted at a second location in said pericardial space, said second catheter for withdrawing at least a portion of said cooled fluid from said pericardial space.

9. The method according to claim 1, further comprising a step of withdrawing at least a portion of said cooled fluid from said pericardial space.

10. The method according to claim 9 wherein said step of withdrawing said cooled fluid includes suction of said fluid from said pericardial space.

11. The method according to claim 9 wherein said suction is at predetermined intervals, corresponding with said delivery of said cooled fluid.

* * * * *